United States Patent [19]

Dearman et al.

[11] Patent Number: 5,241,955
[45] Date of Patent: Sep. 7, 1993

[54] BREATHING APPARATUS

[75] Inventors: Peter T. Dearman, Bishop's Stortford; Richard Smith, Braintree, both of United Kingdom

[73] Assignee: Neotronics Medical Limited, Bishop's Stortford, United Kingdom

[21] Appl. No.: 784,393

[22] PCT Filed: Jan. 7, 1991

[86] PCT No.: PCT/GB91/00019

§ 371 Date: Dec. 31, 1991

§ 102(e) Date: Dec. 31, 1991

[87] PCT Pub. No.: WO91/10463

PCT Pub. Date: Jul. 25, 1991

[30] Foreign Application Priority Data

Jan. 8, 1990 [GB] United Kingdom ............... 9000371

[51] Int. Cl.$^5$ .................................. A61M 16/00
[52] U.S. Cl. ........................ 128/204.18; 128/205.24
[58] Field of Search .................... 128/204.18, 205.24, 128/205.13, 205.15, 204.29; 137/908

[56] References Cited

U.S. PATENT DOCUMENTS

| 2,121,311 | 6/1938 | Anderson et al. | 128/204.27 |
|---|---|---|---|
| 3,362,404 | 1/1968 | Beasley | 128/200.21 |
| 3,434,471 | 3/1969 | Liston | 128/203.19 |
| 3,494,376 | 2/1970 | Doeringsfeld et al. | 137/624.14 |
| 3,522,816 | 8/1970 | Springer | 137/805 |
| 3,662,751 | 5/1972 | Barkalow et al. | 128/204.25 |
| 3,672,366 | 6/1972 | Burchell et al. | 128/205.24 |
| 3,889,669 | 6/1975 | Weigl | 128/204.18 |
| 3,974,828 | 8/1976 | Bird | 128/204.25 |
| 3,985,131 | 10/1976 | Buck | 128/205.24 X |
| 4,127,123 | 11/1978 | Bird | 128/204.25 |
| 4,197,843 | 4/1980 | Bird | 128/200.14 |
| 4,202,330 | 5/1980 | Jariabka | 128/204.18 |
| 4,211,221 | 7/1980 | Schwanbom | 128/204.26 |
| 4,351,329 | 9/1982 | Ellestad et al. | 128/204.21 |
| 4,592,349 | 6/1986 | Bird | 128/204.25 |
| 4,838,257 | 6/1989 | Hatch | 128/204.18 |
| 5,038,770 | 8/1991 | Perkins | 128/204.18 |
| 5,038,774 | 8/1991 | Chabert | 128/205.24 |
| 5,040,529 | 8/1991 | Zalkin | 128/204.18 |
| 5,072,728 | 12/1991 | Pasternack | 128/204.18 |

FOREIGN PATENT DOCUMENTS

| 0190856 | 3/1991 | European Pat. Off. |
| 2133850 | 4/1972 | France |
| 6805142 | 10/1968 | Netherlands |
| WO91/10463 | 7/1991 | PCT Int'l Appl. |
| 1533548 | 11/1978 | United Kingdom |
| 1533550 | 11/1978 | United Kingdom |
| 2162429A | 2/1986 | United Kingdom |
| 2170409B | 5/1988 | United Kingdom |

Primary Examiner—Edgar S. Burr
Assistant Examiner—Eric P. Raciti
Attorney, Agent, or Firm—Kerkam, Stowell, Kondracki & Clarke

[57] ABSTRACT

A breathing apparatus is described for supplying pulses of a breathable gas to a patient; the apparatus comprises a gas inlet (10) connectable to a source of breathable gas, an outlet (37) connectable to provide gas to the patient, a gas flow passage (14,15,34,36) extending between the inlet and the outlet, a main valve (16) located in the gas flow passage for interrupting the flow of gas to the outlet, a throttle (38) in the flow passage downstream of the main valve, a gas reservoir (42) and a valved duct (40,44) connected to supply gas to the reservoir from the part of the flow passage between the main valve and the throttle; the main valve includes a piston (24) that is slidable within a cylinder (22) to open and close the gas flow passage, which piston is biassed in one direction by a resilient member (28) and biassed in the other direction by the gas pressure within the reservoir. When the main valve is open and gas flows from the source to the patient, gas leaks into the reservoir along valved duct (40,44), thereby increasing the pressure in the reservoir (42); this continues until the pressure in the reservoir is sufficient to overcome the spring (28) when the piston moves to close off the gas flow passage. Gas can leak via the valved duct (40, 44) into the flow passage until the pressure in the reservoir falls to a level that allows the spring to move the piston to re-open the flow passage.

6 Claims, 3 Drawing Sheets

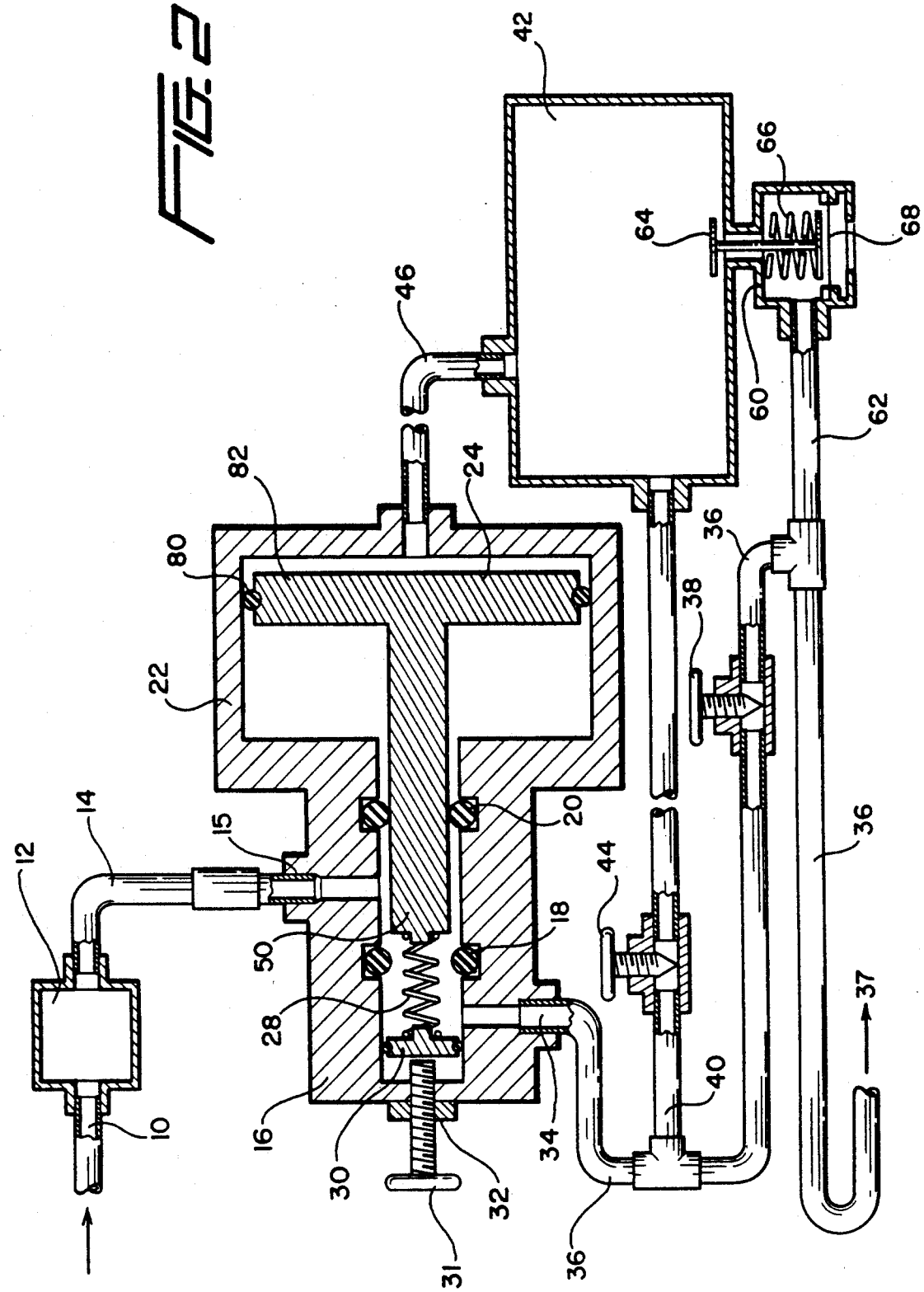

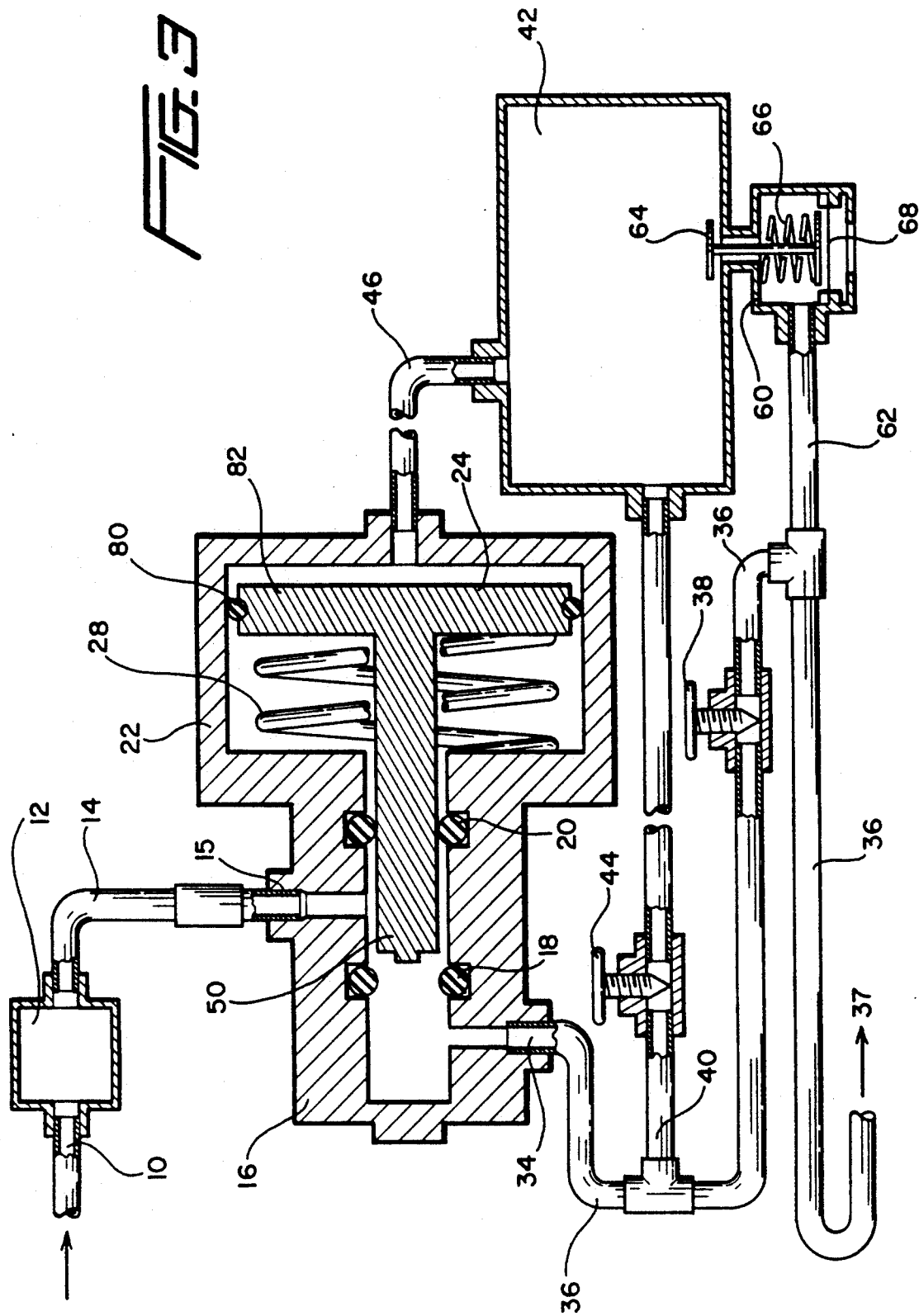

BREATHING APPARATUS

TECHNICAL FIELD

The present invention relates to a breathing apparatus for supplying pulses of breathable gas to a patient, e.g. for emergency resuscitation or as a ventilator for patients during anesthesia.

BACKGROUND ART

GB-2,170,409 describes a breathing apparatus including a gas passage having an inlet to receive gas, an outlet to pass gas to the patient and a valve in the passage to control the flow of gas to provide the desired pulsed flow of gas. A variable throttle is included downstream of the valve which, when gas is flowing in the passage, diverts part of it into a reservoir. The reservoir includes a leak valve which allows gas to leak from the reservoir to atmosphere and a check valve that prevents gas in the reservoir from returning to the gas supply system of the apparatus. The valve includes a piston for opening and closing the valve; the piston is biassed (a) by pressure in the reservoir to move in one direction and (b) by a spring to move in the opposite direction. When the valve is open, gas flows through the passage to the patient, who inhales; at the same time, gas is diverted into the reservoir from the passage at a faster rate than it leaks out of the reservoir through the leak valve and so the pressure in the reservoir increases until it reaches a value at which it can move the piston to close the main valve causing the flow of gas to the patient to the patient to cease, allowing him to exhale (expiratory period). Since there is no gas flowing through the passage, no gas is diverted into the reservoir and the leakage of gas through the leak valve to atmosphere causes the pressure in the reservoir to fall; when the pressure reaches such a low level that the force it exerts on the piston is less than that exerted by the spring, the spring moves the piston to open the valve and resume the flow of gas in the passage thereby causing the patient to inhale once more (inspiratory period). The cycle of the inspiratory expiratory periods are repeated for as long as required. In order to adjust the duration of the inspiratory and expiratory periods, the leak valve needs to be made as a needle valve and a further needle valve needs to be provided in the duct diverting gas into the reservoir.

DISCLOSURE OF THE INVENTION

The present invention provides a simpler arrangement than that described above.

According to the present invention, there is provided a breathing apparatus for supplying pulses of a breathable gas to a patient, which apparatus comprises a gas inlet connectable to a source of breathable gas, an outlet connectable to provide gas to the patient, a gas flow passage extending between the inlet and the outlet, a main valve located in the gas flow passage for interrupting the flow of gas to the outlet, a throttle in the flow passage downstream of the main valve, a gas reservoir and a valved duct connected to supply gas to the reservoir from the part of the flow passage between the main valve and the throttle, wherein the main valve includes a piston that is slidable within a cylinder to open and close the gas flow passage, which piston is biassed in one direction by a resilient member (which will usually be a spring) and biassed in the other direction by the gas pressure within the reservoir, wherein gas in the reservoir can leak out of the reservoir when the flow of gas in the flow passage is interrupted by the main valve, which leakage occurs to the said flow passage, preferably through the said valved duct and thus does not occur directly to ambient atmosphere.

The force exerted on the piston by the resilient member is preferably adjustable since in this way it is possible to alter the ratio of (a) the duration of the period in which the main valve is open and gas is supplied to the patient (the inspiratory phase) to (b) the duration of the period in which the main valve is closed allowing the patient to exhale (the expiratory phase). In a preferred embodiment the resilient member biases the piston to a position in which the gas flow passage is open.

Because the leakage occurs to the flow passage rather than to the atmosphere, the gas is all supplied to the patient and not wasted by being leaked to atmosphere. Furthermore the present invention overcomes a disadvantage of the prior art namely that the leakage path can become blocked because its outlet is to the ambient atmosphere and therefore exposed to entry by foreign matter. In the preferred embodiment in which the leakage occurs through the valved duct, the same valve can be used to control the leakage as is used to control the flow of gas into the reservoir, thereby saving on costs because the prior art requires two separate valves for this purpose (as well as a check valve preventing gas in the reservoir re-entering the system).

BRIEF DESCRIPTION OF THE DRAWINGS

The present invention will now be described by way of example only with reference to the accompanying drawings in which:

FIG. 2 is a view taken partly in cross-section of a second embodiment of the present invention, and FIG. 3 is a view taken partly in cross-section of a third embodiment of the present invention,

BEST MODES FOR CARRYING OUT THE INVENTION

Figure 1:
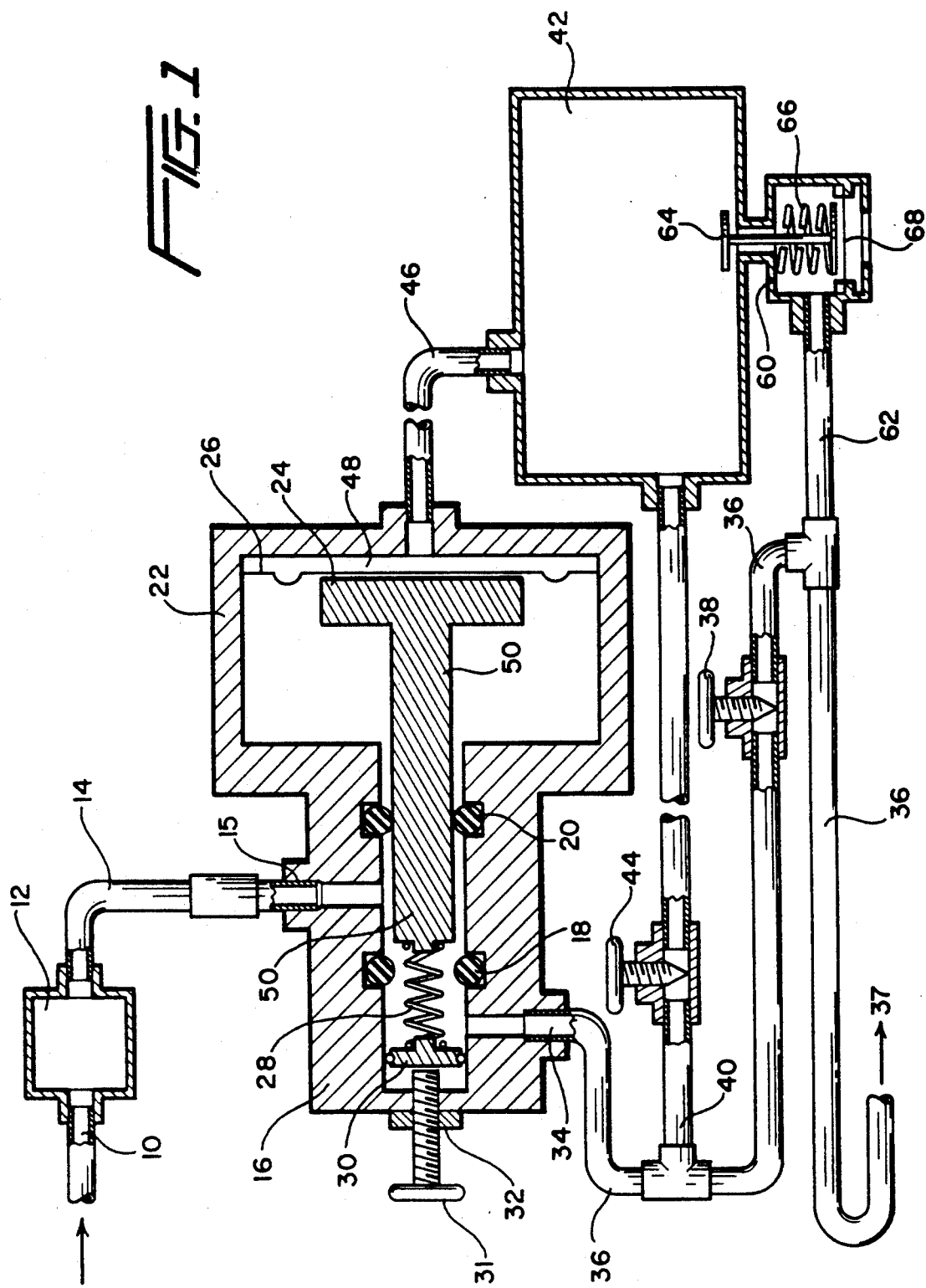
FIG. 1 is a view taken partly in cross-section of one embodiment of the present invention.

Referring to FIG. 1 of the accompanying drawings, breathable gas (e.g. oxygen or air) is supplied via a duct 10 from a source (not shown but which typically is a gas cylinder or a compressor) to a pressure regulator 12 to provide gas to a line 14 at 40 p.s.i. (275 kN/m$^2$). Line 14 is connected to a an inlet 15 in a main valve 16 and supplies gas to a portion of the valve between two O-rings 18 and 20. The valve 16 includes a housing 22, a piston 24 that is slidable within the housing, a diaphragm 26 which engages one end of the piston 24 and a spring 28 which engages the other end of the piston and acts between the piston, an adjusting screw 31 extending through the housing 22 and a cap 30 holding one end of the spring 28; the adjusting screw 31 is held in position by a locking nut 32 and is used to alter the force exerted by the spring on the poston. A valve outlet 34 is located beyond O-ring 18 and conducts gas out of the valve 16 into a duct 36 which leads to an outlet 37 for supplying gas to a patient via the usual patient valve (not shown). A throttle flow valve 38 is included in duct 36. The spring 28 serves as a means to operate the main valve to selectively interrupt the flow of gas.

A branch duct 40 leads off duct 36 and supplies gas from duct 36 to a reservoir 42 via a needle valve 44. The reservoir is connected by a duct 46 to a chamber 48 on the side of the diaphragm 26 remote from the piston 24. The duct 46 has the illustrated reservoir passageway disposed therein, this passageway connected to the reservoir 42 as shown.

In the position shown in FIG. 1, the breathable gas can flow into the valve 16 via inlet 15, past O-ring 18 and out through the valve outlet 34 into duct 36 and from there to outlet 37 of the apparatus and then to the patient so that the patient is caused to inhale (inspiratory phase). The throttle 38 provides a back-pressure in the duct 36 so that gas also flows along the branch duct 40 into the reservoir 42 at a rate determined by the setting of the needle valve 44. The pressure in the reservoir thus increases until it reaches a level at which it exerts a force on the piston 24 (via the diaphragm 26) that is greater than the force exerted by the spring 28 and the frictional force required to move the piston and the piston then moves to the left (as seen in FIG. 1) causing the rod 50 of the piston 24 to contact O-ring 18 thereby sealing off the valve inlet 15 and so preventing gas flow to the valve outlet 34. The closing of the valve 16 terminates the inspiratory phase and allows the patient to exhale (i.e. initiating the expiratory phase).

During the expiratory phase, the gas pressure in the reservoir is higher than in the duct 36 and gas leaks from the reservoir into the duct 36 at a rate determined by the setting of the needle valve 44. When the force resulting from the pressure in the reservoir 42 has fallen to a level that the force exerted by the spring 28 on the piston is greater than the force resulting from the pressure in the reservoir 42 together with the frictional force required to move the piston, the piston moves to the right and so returns to the position shown in FIG. 1, thereby terminating the expiratory phase and initiating the inspiratory phase once again.

It is generally desirable that the ratio of the duration of the inspiratory phase to the duration of the expiratory phase is between 1.6:1 and 2.4:1 and ideally it should be about 2:1; this ratio can be achieved by adjusting the tension in the spring 28 by screwing in or screwing out the adjuster screw 31.

The number of inspiratory/expiratory cycles per minute that is desirable to provide depends on the body weight of the patient; an adult, for example, requires a much lower rate than a child. The number of cycles per minute can be determined by the setting of the needle valve 44; a relatively wide opening of the needle valve means that the pressure level in the reservoir needed to change from the inspiratory phase to the expiratory phase will be established relatively quickly and the leakage of gas from the reservoir will also occur relatively quickly so that the inspiratory and expiratory phases are short and there are a relatively high number of cycles per minute. Likewise, a relatively small opening of the needle valve 44 will produce longer inspiratory and expiratory phases and so the number of cycles per minute will be relatively low.

We have found that the ratio of the duration of the inspiratory phase to the duration of the expiratory phase is relatively constant with a change in the setting of the needle valve 44.

The system can allow gas to be supplied to the patient if he gasps for breath during the expiratory phase. A valve housing 60 is connected by a side duct 62 to the duct 36 downstream of the throttle 38 and includes a valve 64 communicating with the reservoir 42. The housing is open at its base so that the lower surface of the diaphragm 68 is exposed to atmospheric pressure. The valve is biassed by a spring 66 so that it is normally closed but it can be opened by the flexing of a diaphragm 68 when the pressure in the housing 60 falls as a result of the patient gasping for breath. When the valve 64 opens, gas in the reservoir is supplied to the patient along ducts 62 and 36, thereby reducing the pressure in the reservoir and so causing the main valve 22 to open and this initiates the inhalation phase. Once the pressure in the valve housing 60 rises as a result of the commencement of normal gas flow, the valve 64 closes.

The apparatuses shown in FIGS. 2 and 3 are generally similar to that of FIG. 1 and so the same reference nubers have been used to indicate the same features in the three embodiments; the arrangement of FIG. 2 differs from that of FIG. 1 in that the the head of the piston 24 has a larger diameter in the arrangement of FIG. 2 and the diaphragm 26 is replaced by an O-ring 80 forming a seal between the head 82 of the piston 24 and the valve housing 22. In the apparatus of FIG. 3, the bias on the piston 24 is fixed which allows the spring 28 to to be positioned between the head 82 of the piston and the housing 22. The operation of the arrangements of FIGS. 2 and 3 will be apparent from the description of the arrangement of FIG. 1 and so it will not be repeated.

As compared to the apparatus of GB-2,170,409, the apparatus of the present invention has the following advantages:

(1) It dispenses with the individual reservoir leak valve and the non-return check valve in the reservoir required by GB-2,170,409, thereby making the present apparatus cheaper and simpler to manufacture, (2) all the gas is supplied to the patient (in GB 2,170,409, the gas vented through the reservoir leak valve is lost), and (3) the inspiratory/expiratory ratio is set mechanically by spring 28 and does not depend on a valve leaking to atmosphere which, because it is exposed, can become blocked.

As shown in FIG. 1, the reservoir is constructed and connected such that any gas leaving the reservoir necessarily remains within the apparatus unless it passes out said gas inlet or passes out said outlet.

We claim:

1. A breathing apparatus for supplying pulses of a breathable gas to a patient, which apparatus comprises a gas inlet (10), an outlet (37) connectable to provide gas to the patient, a gas flow passage (14, 15, 34, 36) extending between the gas inlet and the outlet, a main valve (16) located in the gas flow passage, and means to operate said main valve to selectively interrupt the flow of gas to the outlet, a throttle (38) in the flow passage downstream of the main valve, a gas reservoir (42) and a valved duct (40, 44) connected to supply gas to the reservoir from a part of the flow passage between the main valve and the throttle, said valved duct having a passageway therein, wherein the main valve includes a piston (24) and a cylinder (22), said piston slidable within said cylinder (22) to open and close the gas flow passage, said means to operate including a resilient member (28) biasing the piston in one direction, further comprising a reservoir passageway connecting said reservoir to said main valve such that gas pressure within the reservoir biases the piston in a direction opposite said one direction, and wherein in use:

when the main valve is open, gas flows into the reservoir from the gas flow passage via the passageway in the valved duct; and when the flow of gas in the gas flow passage is interrupted by closing of said main valve, gas in the reservoir bleeds out of the reservoir via the passageway in the valved duct.

2. A breathing apparatus as claimed in claim 1, characterised in that it includes means (30, 31) for adjusting the force exerted on the piston by the resilient member thereby setting the ratio of (a) the duration of the period in which the main valve is open and gas is supplied to the patient (the inspiratory phase) to (b) the duration of the period in which the main valve is closed allowing the patient to exhale (the expiratory phase).

3. A breathing apparatus as claimed in claim 1, characterised in that it includes means for adjusting the gas flow resistance of the valved duct thereby setting the duration of the pulses of breathable gas.

4. A breathing apparatus as claimed in claim 1, characterised in that the resilient member (28) biases the piston to a position in which the gas flow passage is open.

5. A breathing apparatus as claimed in claim 1 wherein the reservoir is constructed and connected such that any gas leaving the reservoir necessarily remains within the apparatus unless it passes out said gas inlet or passes out said outlet.

6. A breathing apparatus as claimed in claim 1 wherein said reservoir is constructed and connected to avoid venting gas into the atmosphere.

* * * * *